United States Patent [19]

Jollow et al.

[11] 4,265,909

[45] May 5, 1981

[54] INHIBITING PLATELET AGGREGATION WITH SUBSTITUTED ACETANILIDES

[76] Inventors: David J. Jollow, 716 North Shore Dr., Charlestown, S.C. 29412; Perry V. Halushka, 1391 Cecilia Dr., Charlestown, S.C. 29407

[21] Appl. No.: 9,911

[22] Filed: Feb. 6, 1979

Related U.S. Application Data

[62] Division of Ser. No. 919,282, Jun. 26, 1978.

[51] Int. Cl.³ .......................................... A61K 31/165
[52] U.S. Cl. ..................................................... 424/324
[58] Field of Search ......................................... 424/324

[56] References Cited

PUBLICATIONS

Focella et al., Canadian Journal of Chem.

Primary Examiner—Stanley J. Friedman

Attorney, Agent, or Firm—George A. Loud

[57] ABSTRACT

This invention relates to a method for treating mammals to inhibit platelet aggregation which includes administering to mammals a therapeutically effective amount of a compound of the general formula:

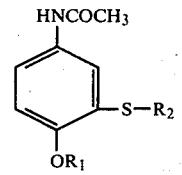

wherein each of $R_1$ and $R_2$ represents a hydrogen atom or a lower alkyl group having from one to three carbon atoms.

2 Claims, No Drawings

INHIBITING PLATELET AGGREGATION WITH SUBSTITUTED ACETANILIDES

The invention described and claimed in this application was made as a result of work supported, in part, by Grant No. GM20387 of the National Institute of Health, Department of Health, Education and Welfare.

This is a division of application Ser. No. 919,282, filed June 26, 1978.

BACKGROUND

Compounds structurally related to acetanilide such as acetaminophen and phenacetin are well known to be effective analgesics and antipyretics in man and other mammals. However, a significant adverse effect associated with this group of compounds is cytotoxicity, e.g. acetaminophen is known to cause fulminant hepatic necrosis and phenacetin to cause both hepatic and renal damage in mammals. This invention relates to a chemical modification of this group of compounds to reduce the toxicity yet retain desirable and effective analgetic and/or antipyretic activity.

A compound used in the present invention, 4-methylthioacetaminophen, has been previously identified as a metabolite of phenacetin, but has not been reported to have any biological activity (see article by A. Focella et al, 50 Canadian Journal of Chemistry 2025 (1972)).

DESCRIPTION OF INVENTION

The present invention is directed to a method for using a composition containing compounds structurally related to acetaminophen (4-hydroxyacetanilide) and phenacetin (4-ethoxyacetanilide) which retain analgesic and/or antipyretic activity but lack the significant cytotoxicity of the parent compounds. The pharmaceutically active ingredient of the compositions of the present invention may be represented by the general formula:

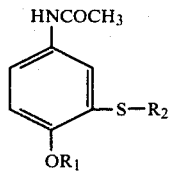

wherein each of $R_1$ and $R_2$ represents a hydrogen atom or a lower alkyl group having from one to three carbon atoms. Preferably, $R_1=H$ and $R_2=CH_3$. Synthesis of the compounds is as described in the Focella article cited above.

More specifically, the present invention is directed to the use of these compounds for analgesic and antipyretic purposes in mammals, which comprises administering the compounds internally to mammals in a pharmaceutically effective amount. The preferred routes for administration of these compounds are by mouth and parenterally, however, other routes may also be employed. For oral administration, the substances are usually prepared in pharmaceutical dosage forms such as tablets, capsules, elixirs, solutions or the like. In preparing dosage units intended for oral administration the active compound is usually mixed with a pharmaceutically-acceptable carrier, also referred to as an excipient. Commonly employed excipients include, for example, starch, gums, alcohols, sugars, fatty acids, etc. For parenteral administration, the compounds are administered in the form of an aqueous parenteral solution, generally admixed with conventional buffering agents, preservatives, etc.

It is believed that dosages in an amount of 1 to 30 mg/kg body weight will be effective in a pharmaceutically acceptable dosage form as mentioned above. The exact dosage may vary depending on the circumstances of administration such as for example the species of mammal, age of mammal, condition treated, severity of the condition and route of administration.

In tests for determining potency, 3-methylthio-4-hydroxyacetanilide was found to be equipotent with aspirin and more potent than acetaminophen for analgesia as estimated in mice using the Writhing test (see E. T. Eckhardt et al. 98 Proc.Soc.Exp. Biol.Med. 186(1958); R. I. Tabor et al. 169 J.Pharmacol.Exp.-Therap. 29(1969)).

The $ED_{50}$ doses using the Horn method (see H. J. Horn 12 Biometrics 311(1956) were 21.5 mg/kg for aspirin and 21.5 mg/kg for methylthio-4-hydroxyacetanilide.

Using the Lichfield-Wilcoxon method (see J. T. Litchfield and F. Wilcoxon, 96 J.Pharmacol.Exp.-Therap. 99(1949). 3-methylthio-4-hydroxyacetanilide was 1.78 times more active than acetaminophen.

Potency for causing hepatic necrosis was tested in Golden Syrian hamsters (see J. R. Mitchell et al. 187 J.Pharmacol.Exp.Therap. 185(1973). Acute administration of acetaminophen caused centrolobular hepatic necrosis at doses above 250 mg/kg (ip). The severity of the lesion was dose-dependent, e.g. cell death occurred in greater than 90% of liver parenchymal cells at doses above 400 mg/kg (ip). On the other hand, hamsters receiving 3-methylthio-4-hydroxyacetanilide showed no evidence of centrolobular hepatic necrosis after doses of 300, 500, and 700 mg/kg (ip).

These test results indicate that compounds of the general structure indicated above possess the same effective analgesic activity as known acetanilide derivatives (acetaminophen, phenacetin) yet lack the capacity to cause hepatic necrosis seen with these currently used analgesics.

Further, in preliminary studies on isolated human platelets, methylthioacetaminophen has also shown significant platelet antiaggregatory activity. Using a 5 min. pre-incubation period, $10^{-5}$ M methylthioacetaminophen totally inhibited in vitro arachidonate induced platelet aggregation whereas $10^{-5}$ M acetaminophen was without significant effect. Such activity indicates that the compound could also be useful as an antithrombotic, antiplatelet agent for therapy in stroke, myocardial infarction, transient ischemic attacks, and other thrombotic and cardiovascular related diseases.

I claim:

1. a method of inhibiting platelet aggregation in mammals comprising administering to said mammals a therapeutically effective amount of a compound of the general formula:

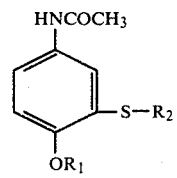

wherein each of $R_1$ and $R_2$ represents a hydrogen atom or a lower alkyl group having from one to three carbon atoms.

2. The method of claim 1 wherein $R_1=H$ and $R_2=CH_3$.

* * * * *